(12) United States Patent
Tojo et al.

(10) Patent No.: US 8,148,566 B2
(45) Date of Patent: *Apr. 3, 2012

(54) METHOD FOR PRODUCING A DIALKYL CARBONATE AND A DIOL

(75) Inventors: Masahiro Tojo, Kurashiki (JP); Hironori Miyaji, Kurashiki (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 210 days.

This patent is subject to a terminal disclaimer.

(21) Appl. No.: 12/626,444

(22) Filed: Nov. 25, 2009

(65) Prior Publication Data

US 2010/0076213 A1    Mar. 25, 2010

Related U.S. Application Data

(62) Division of application No. 10/594,671, filed as application No. PCT/JP2005/011107 on Jun. 17, 2005, now Pat. No. 7,645,896.

(30) Foreign Application Priority Data

Jun. 17, 2004 (JP) ................................ 2004-179799

(51) Int. Cl.
  *C07C 69/96*  (2006.01)
(52) U.S. Cl. ....................................................... 558/277
(58) Field of Classification Search .................. 558/277
  See application file for complete search history.

(56) References Cited

U.S. PATENT DOCUMENTS

| | | |
|---|---|---|
| 3,642,858 A | 2/1972 | Frevel et al. |
| 3,803,201 A | 4/1974 | Gilpin et al. |
| 4,062,884 A | 12/1977 | Romano et al. |
| 4,181,676 A | 1/1980 | Buysch et al. |
| 4,307,032 A | 12/1981 | Krimm et al. |
| 4,661,609 A | 4/1987 | Knifton |
| 4,681,967 A | 7/1987 | Green |
| 4,691,041 A | 9/1987 | Duranleau et al. |
| 4,734,518 A | 3/1988 | Knifton |
| 5,847,189 A | 12/1998 | Tojo et al. |
| 6,346,638 B1 | 2/2002 | Tojo et al. |
| 6,479,689 B1 | 11/2002 | Tojo et al. |
| 7,645,896 B2 * | 1/2010 | Tojo et al. .................... 558/277 |

FOREIGN PATENT DOCUMENTS

| | | |
|---|---|---|
| EP | 1 174 406 A1 | 1/2002 |
| JP | 54-63023 A | 5/1979 |
| JP | 54-148726 A | 11/1979 |
| JP | 55-64550 A | 5/1980 |
| JP | 55-64551 A | 5/1980 |
| JP | 56-10144 A | 2/1981 |
| JP | 63-238043 A | 10/1988 |
| JP | 4-198141 A | 7/1992 |
| JP | 4-230243 A | 8/1992 |
| JP | 5-213830 A | 8/1993 |
| JP | 6-9507 A | 1/1994 |
| JP | 2002-308804 A | 10/2002 |
| JP | 2002-371037 A | 12/2002 |
| JP | 2004-131394 A | 4/2004 |

* cited by examiner

*Primary Examiner* — Rei-tsang Shiao

(74) *Attorney, Agent, or Firm* — Birch, Stewart, Kolasch & Birch, LLP

(57) ABSTRACT

A method for producing a dialkyl carbonate and a diol, comprising: (a) effecting a transesterification reaction between a cyclic carbonate and an aliphatic monohydric alcohol in the presence of a transesterification catalyst, thereby obtaining a reaction mixture containing a product dialkyl carbonate and a product diol, (b) withdrawing a dialkyl carbonate-containing liquid from the reaction mixture, followed by separation of the dialkyl carbonate from the dialkyl carbonate-containing liquid, and (c) withdrawing a diol-containing liquid from the reaction mixture, followed by separation of the diol from the diol-containing liquid, wherein the cyclic carbonate contains a cyclic ether in an amount of from 0.1 to 3,000 ppm by weight, and the product dialkyl carbonate contains a carbonate ether of not more than 10,000 ppm by weight.

8 Claims, 1 Drawing Sheet

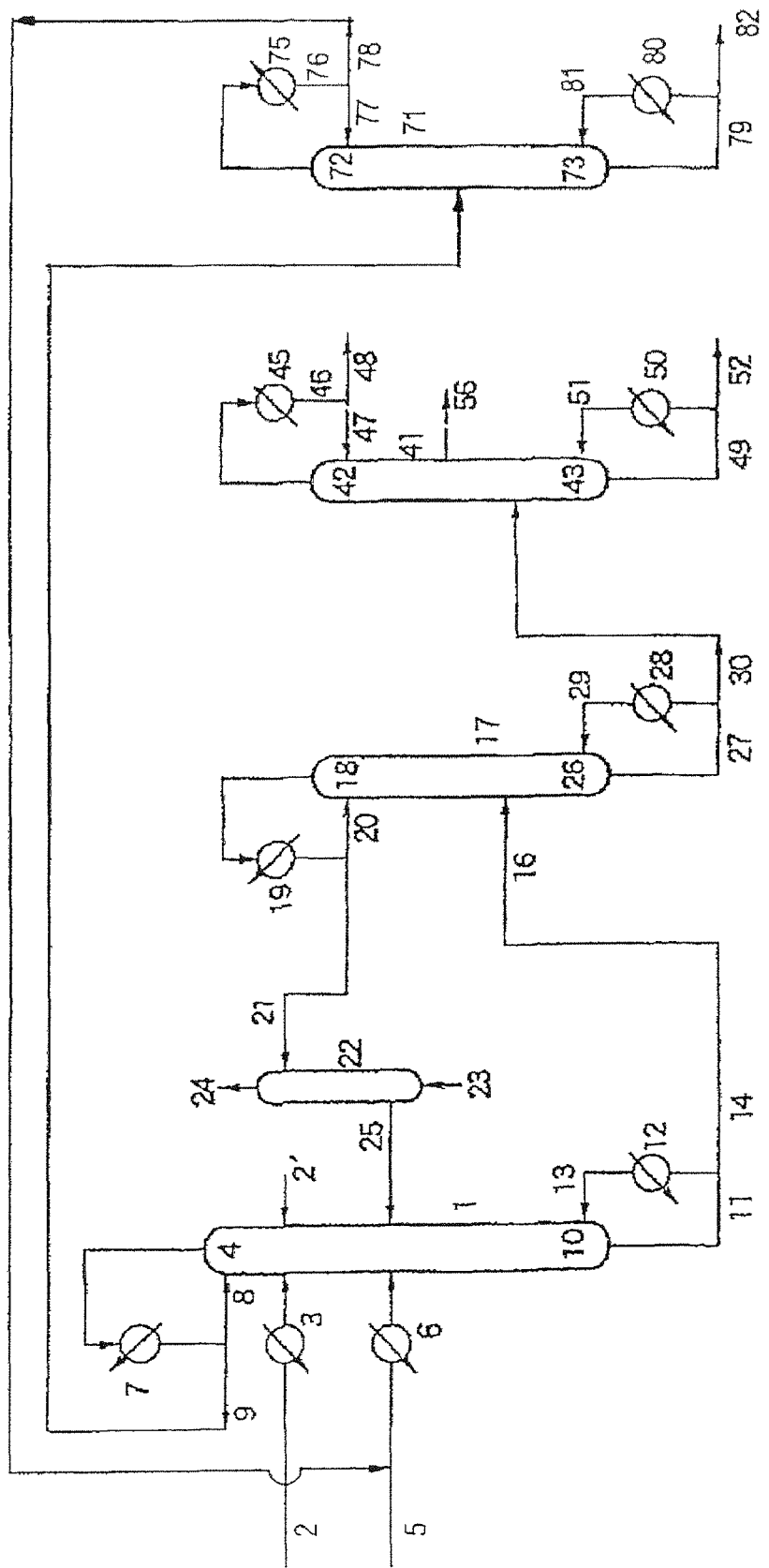

METHOD FOR PRODUCING A DIALKYL CARBONATE AND A DIOL

CROSS-REFERENCE

This application is a Divisional of U.S. application Ser. No. 10/594,671, filed on Sep. 28, 2006 now U.S. Pat. No. 7,645,896, which is the national phase of PCT/JP2005/011107 filed on Jun. 17, 2005, which designated the United States and which claims priority to Japanese Application 2004-179799 filed on Jun. 17, 2004. The entire contents of the above applications are hereby incorporated by reference.

FIELD OF THE INVENTION

The present invention relates to a method for producing a dialkyl carbonate and a diol. More particularly, the present invention is concerned with a method for producing a dialkyl carbonate and a diol, comprising: (a) effecting a transesterification reaction between a cyclic carbonate and an aliphatic monohydric alcohol in the presence of a transesterification catalyst, thereby obtaining a reaction mixture containing a product dialkyl carbonate and a product diol, (b) withdrawing a dialkyl carbonate-containing liquid from the reaction mixture, followed by separation of the dialkyl carbonate from the dialkyl carbonate-containing liquid, and (c) withdrawing a diol-containing liquid from the reaction mixture, followed by separation of the diol from the diol-containing liquid, wherein the cyclic carbonate contains a cyclic ether in an amount of from 0.1 to 3,000 ppm by weight, and the product dialkyl carbonate contains a carbonate ether in an amount of not more than 10,000 ppm by weight. In the dialkyl carbonate produced by the method of the present invention, the content of a carbonate ether (which is a conventionally unknown impurity) is reduced to a specific low range. The dialkyl carbonate obtained by the method of the present invention can be used to produce a transesterification aromatic carbonate. The transesterification aromatic carbonate produced can be very advantageously used to produce a colorless, high molecular weight aromatic polycarbonate.

BACKGROUND OF THE INVENTION

With respect to the method for producing a dialkyl carbonate and a diol by reacting a cyclic carbonate with an aliphatic monohydric alcohol, various proposals have been made. Most of those proposals relate to the development of catalysts for the above reaction. Examples of such catalysts include alkali metals or basic compounds containing alkali metals (see Patent Documents 1 and 2), tertiary aliphatic amines (see Patent Document 3), thallium compounds (see Patent Document 4), tin alkoxides (see Patent Document 5), alkoxides of zinc, aluminum and titanium (see Patent Document 6), a mixture of a Lewis acid with a nitrogen-containing organic base (see Patent Document 7), phosphine compounds (see Patent Document 8), quaternary phosphonium salts (see Patent Document 9), cyclic amidines (see Patent Document 10), compounds of zirconium, titanium and tin (see Patent Document 11), a solid, strongly basic anion-exchanger containing a quaternary ammonium group (see Patent Document 12), a solid catalyst selected from the group consisting of a tertiary amine- or quaternary ammonium group-containing ion-exchange resin, a strongly acidic or a weakly acidic ion-exchange resin, a silica impregnated with a silicate of an alkali metal or an alkaline earth metal, and a zeolite exchanged with ammonium ion (Patent Document 13), and a homogeneous catalyst selected from the group consisting of tertiary phosphine, tertiary arsine, tertiary stibine, a divalent sulfur compound and a selenium compound (see Patent Document 14).

With respect to the method for conducting the above-mentioned reaction between a cyclic carbonate and a diol, the below-mentioned four types of methods (1) to (4) have conventionally been proposed. Hereinbelow, explanation is made with respect to such methods (1) to (4), taking as an example the production of dimethyl carbonate and ethylene glycol by the reaction between ethylene carbonate and methanol, which is a representative example of reactions between cyclic carbonates and diols.

First method (hereinafter referred to as "method (1)") is a completely batchwise method in which ethylene carbonate, methanol and a catalyst are fed to an autoclave as a batchwise reaction vessel, and a reaction is performed at a reaction temperature higher than the boiling point of methanol under pressure for a predetermined period of time (see Patent Documents 1, 2 and 5 to 9).

Second method (hereinafter referred to as "method (2)") is a batchwise method, using an apparatus comprising a reaction vessel provided at an upper portion thereof with a distillation column, in which ethylene carbonate, methanol and a catalyst are fed to the reaction vessel, and a reaction is performed by heating the contents of the reaction vessel to a predetermined temperature. In this method, in order to compensate for the methanol distilled as an azeotropic mixture of the methanol and the produced dimethyl carbonate, the continuous or batchwise addition of supplemental methanol to the reaction vessel is optionally conducted. However, irrespective of whether or not such an addition of supplemental methanol is conducted, the reaction per se is performed only in a batch-type reaction vessel. That is, in this method, the reaction is batchwise performed under reflux for a prolonged period of time as long as 3 to 20 odd hours. (Patent Documents 15, 3 and 4).

Third method (hereinafter referred to as "method (3)") is a liquid flow method in which a solution of ethylene carbonate in methanol is continuously fed to a tubular reactor to perform a reaction at a predetermined reaction temperature in the tubular reactor, and the resultant reaction mixture in a liquid form containing the unreacted materials (i.e., ethylene carbonate and methanol) and the reaction products (i.e., dimethyl carbonate and ethylene glycol) is continuously withdrawn through an outlet of the reactor. This method has conventionally been conducted in two different manners in accordance with the two types of catalyst used. That is, one of the manners consists in passing a mixture of a solution of ethylene carbonate in methanol and a solution of a homogenous catalyst in a solvent through a tubular reactor to perform a reaction, thereby obtaining a reaction mixture, and separating the catalyst from the obtained reaction mixture (see Patent Documents 11 and 14). The other manner consists in performing the reaction in a tubular reactor having a heterogeneous catalyst securely placed therein (see Patent Documents 12 and 13). Since the reaction between ethylene carbonate and methanol to produce dimethyl carbonate and ethylene glycol is an equilibrium reaction, the flow method using a tubular reactor cannot achieve a higher conversion of ethylene carbonate than the conversion of ethylene carbonate at the equilibrium state of reaction (the latter conversion depends on the composition ratio of the feedstocks fed to the reactor and the reaction temperature). For example, in Example 1 of Patent Document 11 which is directed to a continuous flow reaction method using a tubular reactor and wherein the flow reaction is conducted at 130° C. using a feedstock mixture having a methanol/ethylene carbonate molar ratio of 4/1, the conversion of ethylene carbonate is only 25%. This means that large amounts of unreacted ethylene carbonate and unreacted methanol, which are contained in the reaction mixture, need to be separated and recovered, which in turn are recycled to the reactor. Actually, in the method disclosed in Patent Document 13, various apparatuses are used for the separation, purification, recovery and recycling of the unreacted compounds.

Fourth method (hereinafter referred to as "method (4)") is a reactive distillation method in which each of ethylene carbonate and methanol is continuously fed to a multi-stage distillation column to perform a reaction in a plurality of stages of the distillation column in the presence of a catalyst, while continuously effecting separation between the produced dimethyl carbonate and the produced ethylene glycol (Patent Documents 16 to 19).

Thus, the conventional methods for producing a dialkyl carbonate and a diol by reacting a cyclic carbonate with an aliphatic monohydric alcohol, can be classified into the following four methods:
(1) A completely batchwise method;
(2) A batchwise method using a reaction vessel provided at an upper portion thereof with a distillation column;
(3) A liquid flow method using a tubular reactor; and
(4) A reactive distillation method.
However, the above-mentioned conventional methods (1) to (4) have their respective problems as described below.

In the case of each of the completely batchwise method (1) and the flow method (3) using a tubular reactor, the maximum conversion of a cyclic carbonate depends on the composition ratio of the feedstocks fed to the reactor and the reaction temperature. Therefore, it is impossible to convert all of the feedstocks into the products and the conversion of the cyclic carbonate becomes low. Further, in the batchwise method (2), for improving the conversion of a cyclic carbonate, the produced dialkyl carbonate must be removed using a largely excess amount of an aliphatic monohydric alcohol, and a long reaction time is needed.

In the case of the reactive distillation method (4), it is possible to perform a reaction with high conversion, as compared to the conversions in methods (1), (2) and (3). However, needless to say, even in the case of method (4), production of a dialkyl carbonate and a diol is performed by a reversible, equilibrium reaction. Accordingly, even when it is possible to achieve a substantially 100% conversion of a cyclic carbonate by method (4), it is impossible to prevent a trace amount of the cyclic carbonate from remaining unreacted in a produced diol. Therefore, for obtaining a high purity diol by method (4), in general, it is necessary to separate the cyclic carbonate from the diol by performing a distillation under strictly controlled conditions. In Patent Document 20, it is attempted to solve this problem by hydrolyzing the unreacted cyclic carbonate to convert it into a diol. Further, in Patent Document 21, it is attempted to solve this problem by reacting the unreacted cyclic carbonate with a diol to convert it into an ether.

In addition, there have been proposed methods in which water or water having an oxygen content of not more than 100 ppm is introduced into the process for distillation purification of a diol, to thereby obtain a high purity diol having high UV transmission or low aldehyde content (see Patent Documents 22 and 23).

In the method for producing a dialkyl carbonate and a diol by reacting a cyclic carbonate with an aliphatic monohydric alcohol, the presence of a carbonate ether described in the pre-sent invention was not known in the art. The present inventors have for the first time found that a dialkyl carbonate obtained by the above-mentioned method contains a carbonate ether and that when a dialkyl carbonate contains a carbonate ether in an amount exceeding a specific level, the reaction using such a dialkyl carbonate as a raw material poses various problems. For example, it has become apparent that when a transesterification aromatic carbonate is produced from such a conventional dialkyl carbonate and phenol, the produced aromatic carbonate will contain impurities.

As can be understood from the above, no method has heretofore been proposed for producing a dialkyl carbonate and a diol from a cyclic carbonate and an aliphatic monohydric alcohol, wherein the produced dialkyl carbonate contains a carbonate ether only in a content which is reduced to a specific low range.

Patent Document 1: U.S. Pat. No. 3,642,858
Patent Document 2: Unexamined Japanese Patent Application Laid-Open Specification No. Sho 54-48715 (corresponding to U.S. Pat. No. 4,181,676)
Patent Document 3: Unexamined Japanese Patent Application Laid-Open Specification No. Sho 51-122025 (corresponding to U.S. Pat. No. 4,062,884)
Patent Document 4: Unexamined Japanese Patent Application Laid-Open Specification No. Sho 54-48716 (corresponding to U.S. Pat. No. 4,307,032)
Patent Document 5: Unexamined Japanese Patent Application Laid-Open Specification No. Sho 54-63023
Patent Document 6: Unexamined Japanese Patent Application Laid-Open Specification No. Sho 54-148726
Patent Document 7: Unexamined Japanese Patent Application Laid-Open Specification No. Sho 55-64550
Patent Document 8: Unexamined Japanese Patent Application Laid-Open Specification No. Sho 55-64551
Patent Document 9: Unexamined Japanese Patent Application Laid-Open Specification No. Sho 56-10144
Patent Document 10: Unexamined Japanese Patent Application Laid-Open Specification No. Sho 59-106436
Patent Document 11: Unexamined Japanese Patent Application Laid-Open Specification No. Sho 63-41432 (corresponding to U.S. Pat. No. 4,661,609)
Patent Document 12: Unexamined Japanese Patent Application Laid-Open Specification No. Sho 63-238043
Patent Document 13: Unexamined Japanese Patent Application Laid-Open Specification No. Sho 64-31737 (corresponding to U.S. Pat. No. 4,691,041)
Patent Document 14: U.S. Pat. No. 4,734,518
Patent Document 15: U.S. Pat. No. 3,803,201
Patent Document 16: Unexamined Japanese Patent Application Laid-Open Specification No. Hei 4-198141
Patent Document 17: Unexamined Japanese Patent Application Laid-Open Specification No. Hei 4-230243
Patent Document 18: Unexamined Japanese Patent Application Laid-Open Specification No. Hei 5-213830 (corresponding to German Patent No. 4,129,316)
Patent Document 19: Unexamined Japanese Patent Application Laid-Open Specification No. Hei 6-9507 (corresponding to German Patent No. 4,216,121)
Patent Document 20: International Publication No. WO 97/23445
Patent Document 21: International Publication No. WO 00/51954
Patent Document 22: Unexamined Japanese Patent Application Laid-Open Specification No. 2002-308804
Patent Document 23: Unexamined Japanese Patent Application Laid-Open Specification No. 2004-131394

DISCLOSURE OF THE INVENTION

Problems to be Solved by the Invention

An object of the present invention is to provide a method for producing a dialkyl carbonate containing a carbonate ether (which is a conventionally unknown impurity) only in an amount which is reduced to a specific low range, wherein the dialkyl carbonate can be used to produce a transesterification aromatic carbonate which can be very advantageously used to produce a colorless, high molecular weight aromatic polycarbonate.

Means to Solve the Problems

In this situation, for solving the above mentioned problems, the present inventors have made extensive and intensive studies. As a result, they have unexpectedly found that, in a method for producing a dialkyl carbonate and a diol, comprising effecting a transesterification reaction between a cyclic carbonate and an aliphatic monohydric alcohol in the presence of a transesterification catalyst, thereby producing a product dialkyl carbonate and a product diol, when the cyclic carbonate as a raw material contains a cyclic ether, a carbonate ether is by produced and enters the dialkyl carbonate produced. They have also found that, by reducing the cyclic ether content of the cyclic carbonate as a raw material, the carbonate ether content of the dialkyl carbonate produced can be reduced. Specifically, the present inventors have found that the above-mentioned problems can be solved by a method for producing a dialkyl carbonate and a diol, comprising: (a) effecting a transesterification reaction between a cyclic carbonate and an aliphatic monohydric alcohol in the presence of a transesterification catalyst, thereby obtaining a reaction mixture containing a product dialkyl carbonate and a product diol, (b) withdrawing a dialkyl carbonate-containing liquid from the reaction mixture, followed by separation of the dialkyl carbonate from the dialkyl carbonate-containing liquid, and (c) withdrawing a diol-containing liquid from the reaction mixture, followed by separation of the diol from the diol-containing liquid, wherein the cyclic carbonate contains a cyclic ether in an amount of from 0.1 to 3,000 ppm by weight, and the product dialkyl carbonate contains a carbonate ether in an amount of not more than 10,000 ppm by weight. Based on these findings, the present invention has been completed.

The foregoing and other objects, features and advantages of the present invention will be apparent from the following detailed description taken in connection with the accompanying drawing, and the appended claims.

Effects of the Invention

In the dialkyl carbonate produced by the method of the present invention, the content of a carbonate ether (which is a conventionally unknown impurity) is reduced to a specific low range. The dialkyl carbonate obtained by the method of the present invention can be used to produce a transesterification aromatic carbonate. The transesterification aromatic carbonate produced can be very advantageously used to produce a colorless, high molecular weight aromatic polycarbonate.

BRIEF DESCRIPTION OF THE DRAWING

FIG. 1 A diagram showing the system which was used for practicing the Examples and Comparative Example of the present application.

DESCRIPTION OF REFERENCE NUMERALS 1 continuous multi-stage distillation column
3, 6 preheater
4, 18, 42, 72 top of column
7, 19, 45, 75 condenser
10, 26, 43, 73 bottom of column
12, 28, 50, 80 reboiler
17 low boiling point mixture separation column
22 carbon dioxide separation column
41 diol (ethylene glycol (EG)) purification column
71 DMC separation column
2, 2', 5, 8, 9, 11, 13, 14, 16, 20, 21, 23, 24, 25, 27, 29, 30, 46, 47, 48, 49, 51, 52, 56, 76, 77, 78, 79, 81, 82 conduit

BEST MODE FOR CARRYING OUT THE INVENTION

According to the present invention, there is provided a method for producing a dialkyl carbonate and a diol, comprising:

(a) effecting a transesterification reaction between a cyclic carbonate and an aliphatic monohydric alcohol in the presence of a transesterification catalyst, thereby obtaining a reaction mixture containing a product dialkyl carbonate and a product diol, (b) withdrawing a dialkyl carbonate-containing liquid from the reaction mixture, followed by separation of the dialkyl carbonate from the dialkyl carbonate-containing liquid, and (c) withdrawing a diol-containing liquid from the reaction mixture, followed by separation of the diol from the diol-containing liquid, the steps (b) and (c) being performed in either order or simultaneously, wherein:

the cyclic carbonate contains a cyclic ether represented by the formula (1) below in an amount of from 0.1 to 3,000 ppm by weight, and the product dialkyl carbonate contains a carbonate ether represented by the formula (2) below in an amount of not more than 10,000 ppm by weight,

(1)

wherein $R^1$ represents a divalent group represented by the formula: —$(CH_2)_m$— wherein m is an integer of from 2 to 6, and at least one hydrogen atom of $R^1$ is optionally replaced by at least one substituent group selected from the group consisting of a $C_{1-10}$ alkyl group and a $C_{6-10}$ aryl group, and $$R^2OR^1OCOOR^2 \qquad (2)$$

wherein $R^1$ is as defined above for formula (1), $R^2$ represents a $C_{1-12}$ monovalent aliphatic group, and at least one hydrogen atom of $R^2$ is optionally replaced by at least one substituent group selected from the group consisting of a $C_{1-10}$ alkyl group and a $C_{6-10}$ aryl group.

For easier understanding of the present invention, the essential features and various preferred embodiments of the present invention are enumerated below.

1. A method for producing a dialkyl carbonate and a diol, comprising:

(a) effecting a transesterification reaction between a cyclic carbonate and an aliphatic monohydric alcohol in the presence of a transesterification catalyst, thereby obtaining a reaction mixture containing a product dialkyl carbonate and a product diol, (b) withdrawing a dialkyl carbonate-containing liquid from the reaction mixture, followed by separation of the dialkyl carbonate from the dialkyl carbonate-containing liquid, and (c) withdrawing a diol-containing liquid from the reaction mixture, followed by separation of the diol from the diol-containing liquid, the steps (b) and (c) being performed in either order or simultaneously, wherein:

the cyclic carbonate contains a cyclic ether represented by the formula (1) below in an amount of from 0.1 to 3,000 ppm by weight, and the product dialkyl carbonate contains a carbonate ether represented by the formula (2) below in an amount of not more than 10,000 ppm by weight,

(1)

wherein $R^1$ represents a divalent group represented by the formula: $-(CH_2)_m-$ wherein m is an integer of from 2 to 6, and at least one hydrogen atom of $R^1$ is optionally replaced by at least one substituent group selected from the group consisting of a $C_{1-10}$ alkyl group and an aryl group, and $$R^2OR^1OCOOR^2 \quad (2)$$

wherein $R^1$ is as defined above for formula (1), $R^2$ represents a $C_{1-12}$ monovalent aliphatic group, and at least one hydrogen atom of $R^2$ is optionally replaced by at least one substituent group selected from the group consisting of a $C_{1-10}$ alkyl group and an aryl group.

2. The method according to item 1 above, wherein the amount of the cyclic ether in the cyclic carbonate is from 3 to 1,500 ppm by weight.

3. The method according to item 2 above, wherein the amount of the cyclic ether in the cyclic carbonate is from 10 to 1,000 ppm by weight.

4. The method according to any one of items 1 to 3 above, wherein the cyclic carbonate is ethylene carbonate.

5. The method according to any one of items 1 to 4 above, wherein the transesterification reaction is performed in a reactive distillation column.

6. A dialkyl carbonate produced by the method of any one of items 1 to 5 above, which contains a carbonate ether represented by the formula (2) of item 1 above in an amount of from 1 to 10,000 ppm by weight.

7. The dialkyl carbonate according to item 6 above, wherein the amount of the carbonate ether in the dialkyl carbonate is from 3 to 5,000 ppm by weight.

8. The dialkyl carbonate according to item 7 above, wherein the amount of the carbonate ether in the dialkyl carbonate is from 10 to 3,000 ppm by weight.

Hereinbelow, the present invention will be explained in detail.

The reaction performed in the present invention is a reversible, equilibrium transesterification reaction represented by the following reaction scheme (I), in which a dialkyl carbonate (C) and a diol (D) are produced from a cyclic carbonate (A) and an aliphatic monohydric alcohol (B):

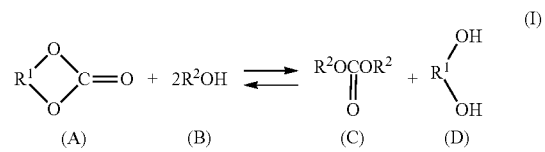
(I)

wherein $R^1$ and $R^2$ are as defined above.

In the present invention, the reason why the carbonate ether content of the product dialkyl carbonate is reduced to a specific low range has not yet been fully elucidated. However, it is considered that a carbonate ether is generated in the reaction system by the reaction between a cyclic ether and an aliphatic monohydric alcohol or a carbonate and, therefore, the amount of generated carbonate ether can be reduced by lowering the cyclic ether content of the cyclic carbonate.

In the present invention, the transesterification reaction can be performed by a conventional transesterification reactor. With respect to the transesterification reactor used in the method of the present invention, there is no particular limitation, and there can be used any of various conventional types of reactors, such as a reactor comprising a combination of a fixed bed reactor and a distillation column, an agitation vessel, a multi-stage agitation type reactor comprising multiple agitation vessels, a multi-stage distillation column, and a combination of the above-mentioned reactors. These reactors can be used in either a batchwise manner or a continuous manner. From the viewpoint of displacing the equilibrium of the reaction toward the product system, a multi-stage distillation column is preferred, and a continuous multi-stage distillation column is more preferred. With respect to the multi-stage distillation column, there is no particular limitation as long as it is a distillation column which has two or more stages of distillation and which is capable of continuous distillation. In the present invention, the term "stages" is intended to include theoretical stages (theoretical plates). In the case of a distillation column having no substantive stages, such as a packed column, the value obtained by dividing the packing height by the height per theoretical stage (plate) (H.E.T.P.) (height equivalent to a theoretical plate) is considered as the number of stages.

Examples of such continuous multi-stage distillation columns include plate type columns using a tray, such as a bubble-cap tray, a sieve tray, a valve tray or a counterflow tray, and packed type columns packed with various packings, such as a Raschig ring, a Lessing ring, a Pall ring, a Berl saddle, an Interlox saddle, a Dixon packing, a McMahon packing, a Heli pack, a Sulzer packing and Mellapak. Any column which is generally used as a continuous multi-stage distillation column can be utilized. Further, a mixed type of plate column and packed column, which comprises both a plate portion and a portion packed with packings, can also be preferably used. When a solid catalyst which is insoluble in the liquid phase in a distillation column is used, a packed column type distillation column, in which the solid catalyst is used in substitution for part or all of the packings, is preferably employed. As the continuous multi-stage distillation column to be used in the method of the present invention, the above-mentioned distillation columns can be used individually or in combination.

When used in combination, a plurality of distillation columns may be connected in series or in parallel.

A cyclic carbonate used as a raw material in the method of the present invention is represented by formula (A) in reaction scheme (I) mentioned above. Examples of cyclic carbonates include alkylene carbonates, such as ethylene carbonate and propylene carbonate, 1,3-dioxacyclohexa-2-one, 1,3-dioxacyclohepta-2-one, and the like. Of these cyclic carbonates, ethylene carbonate and propylene carbonate are preferred because of their good availability. Ethylene carbonate is most preferred.

In the cyclic carbonate used in the present invention, the content of a cyclic ether represented by the formula (1) above is preferably 3,000 ppm or less. The lower the cyclic ether content of the cyclic carbonate, the lower the carbonate ether content of the dialkyl carbonate produced. However, for producing a cyclic carbonate having extremely low cyclic ether content, the cyclic carbonate must be produced by a method employing a special purification method. Therefore, in the present invention, the cyclic ether content of the cyclic carbonate is in the range of from 0.1 to 3,000 ppm, preferably from 1 to 3,000 ppm, more preferably from 3 to 1,500 ppm, most preferably from 10 to 1,000 ppm.

With respect to the cyclic ether content of a cyclic carbonate obtained in the prior art, attention is drawn to the following. When ethylene carbonate (which is a cyclic carbonate) is produced from ethylene oxide (which is a cyclic ether), it is generally known that the conversion of ethylene oxide is 99.0%, and the selectivity for ethylene carbonate is 99.2% (see, e.g., U.S. Pat. Nos. 4,166,773, 4,786,741 and 4,314,945). That is, in the prior art, the ethylene carbonate (cyclic carbonate) produced inevitably contains about 5,000 ppm of ethylene oxide (cyclic ether) which remains unreacted. Therefore, in the prior art, it is impossible to obtain the cyclic carbonate used in the method of the present invention, the cyclic carbonate having the cyclic ether content reduced to the above-mentioned specific range (i.e., 0.1 to 3,000 ppm).

In the present invention, when ethylene carbonate is used as a cyclic carbonate, the ethylene carbonate can be produced by reacting ethylene oxide (which is a cyclic ether) with carbon dioxide. As an example of a method for producing ethylene carbonate which has the cyclic ether content reduced to the above-mentioned specific range, there can be mentioned a method in which ethylene carbonate is produced by reacting ethylene oxide with carbon dioxide, wherein the ethylene oxide content of the ethylene carbonate produced is reduced by any of the following methods ($\alpha$) to ($\delta$): ($\alpha$) a method in which a so-called finisher (which is a small reactor) is additionally provided in the production plant for ethylene carbonate, and ethylene oxide is reacted with carbon dioxide at a conversion as high as 99.5% or more while maintaining the selectivity for ethylene carbonate at 99.0% or more; ($\beta$) a method in which, immediately after a reaction mixture containing ethylene carbonate is taken out from the reactor, a portion of the reaction mixture is distilled off to the outside of the reaction system simultaneously with evaporation-off of carbon dioxide gas; ($\gamma$) a method in which, before performing the purification of a reaction mixture containing ethylene carbonate, unreacted ethylene oxide is distilled off from the reaction mixture by using a flash tank or the like; and ($\delta$) a method in which a portion of a column top composition (containing unreacted ethylene oxide) obtained at the top of a distillation column for performing the purification of ethylene carbonate is taken out of the reaction system. The above-mentioned methods ($\alpha$) to ($\delta$) may be used individually; however, from the viewpoint of ease in reducing the cyclic ether content of a cyclic carbonate, it is preferred to use the above-mentioned methods ($\alpha$) to ($\delta$) in combination.

Specific examples of cyclic ethers include ethylene oxide, propylene oxide, oxacyclobutane and oxacyclopentane.

An aliphatic monohydric alcohol used as another raw material in the method of the pre-sent invention is a compound which is represented by formula (B) in reaction scheme (I) mentioned above and has a boiling point lower than that of the diol. The type of an aliphatic monohydric alcohol which can be used in the method of the present invention varies depending on the type of the cyclic carbonate used. Examples of aliphatic monohydric alcohols include methanol, ethanol, propanol (isomers), allyl alcohol, butanol (isomers), 3-butene-1-ol, amyl alcohol (isomers), hexyl alcohol (isomers), heptyl alcohol (isomers), octyl alcohol (isomers), nonyl alcohol (isomers), decyl alcohol (isomers), undecyl alcohol (isomers), dodecyl alcohol (isomers), cyclopentanol, cyclohexanol, cycloheptanol, cyclooctanol, methylcyclopentanol (isomers), ethylcyclopentanol (isomers), methylcyclohexanol (isomers), ethylcyclohexanol (isomers), dimethylcyclohexanol (isomers), diethylcyclohexanol (isomers), phenylcyclohexanol (isomers), benzyl alcohol, phenethyl alcohol (isomers), phenylpropanol (isomers) and the like. The above-mentioned aliphatic monohydric alcohol may be substituted with at least one substituent, such as a halogen atom, a lower alkoxy group, a cyano group, an alkoxycarbonyl group, an aryloxycarbonyl group, an acyloxy group or a nitro group.

Of these aliphatic monohydric alcohols, an alcohol having 1 to 6 carbon atoms is preferred. More preferred are monohydric alcohols having 1 to 4 carbon atoms, i.e., methanol, ethanol, propanol (isomers) and butanol (isomers). When ethylene carbonate or propylene carbonate is used as a cyclic carbonate, methanol and ethanol are preferred, and especially preferred is methanol.

In the method of the present invention, the transesterification reaction is performed in the presence of a transesterification catalyst. The method for causing a transesterification catalyst to be present in the reactor is not particularly limited. For example, a homogeneous catalyst which is soluble in the reaction system under the reaction conditions can be caused to be present in the transesterification reactor by continuously feeding the homogeneous catalyst to the transesterification reactor. Alternatively, a heterogeneous catalyst (solid catalyst) which is insoluble in the reaction system under the reaction conditions, can be caused to be present in the transesterification reactor by packing the solid catalyst in the transesterification reactor. The above-mentioned homogeneous and heterogeneous catalysts can be used in combination.

When a homogeneous catalyst is continuously fed to the transesterification reactor, it may be fed to the reactor together with a feedstock cyclic carbonate and/or a feedstock aliphatic monohydric alcohol. Alternatively, the homogeneous catalyst may be fed to the reactor at a position different from that at which the feedstock is fed. Further, when a multi-stage distillation column is used as a transesterification reactor, the homogeneous catalyst can be fed to the distillation column at any position as long as the position is at least one theoretical stage (plate) above the column bottom.

However, since the region where the reaction actually takes place in the continuous multi-stage distillation column is generally below the position at which the homogeneous catalyst is fed, it is preferred that the homogeneous catalyst is fed to the distillation column at a position between the top of the column and the position at which the feedstock is fed.

When a heterogeneous solid catalyst is used as a catalyst, the catalyst can be packed in a desired amount at a desired position of the reactor. When a multi-stage distillation column is used as a transesterification reactor, the catalyst layer present in the column has a height which corresponds to at least one theoretical stage (plate), preferably two or more theoretical stages (plates). A catalyst which can serve as a packing for the multi-stage distillation column can also be used.

As a transesterification catalyst used in the present invention, various types of known catalysts can be used. Examples of such catalysts include alkali metals or alkaline earth metals, such as lithium, sodium, potassium, rubidium, cesium, magnesium, calcium, strontium and barium; basic compounds, such as hydrides, hydroxides, alkoxides, aryloxides and amides of alkali metals or alkaline earth metals; basic compounds, such as carbonates and hydrogencarbonates of alkali metals or alkaline earth metals and alkali metal or alkaline earth metal salts of organic acids; tertiary amines, such as triethylamine, tributylamine, trihexylamine and benzyldiethylamine; nitrogen-containing heteroaromatic compounds, such as N-alkylpyrrole, N-alkylindole, oxazole, N-alkylimidazole, N-alkylpyrazole, oxadiazole, pyridine, alkylpyridine, quinoline, alkylquinoline, isoquinoline, alkylisoquinoline, acridine, alkylacridine, phenanthroline, alkylphenanthroline, pyrimidine, alkylpyrimidine, pyradine, alkylpyradine, triazine and alkyltriazine; cyclic amidines, such as diazabicycloundecene (DBU) and diazabicyclononene (DBN); thallium compounds, such as thallium oxide, thallium halides, thallium hydroxide, thallium carbonate, thallium nitrate, thallium sulfate and thallium salts of organic acids; tin compounds, such as tributyl-methoxytin, tributylethoxytin, dibutyldimethoxytin, diethyldiethoxytin, dibutyldiethoxytin, dibutylphenoxy-tin, diphenylmethoxytin, dibutyltin acetate, tributyl-tin chloride and tin 2-ethylhexanoate; zinc compounds, such as dimethoxyzinc, diethoxyzinc, ethylenedioxyzinc and dibutoxyzinc; aluminum compounds, such as aluminum trimethoxide, aluminum triisopropoxide and aluminum tributoxide; titanium compounds, such as tetramethoxy-titanium, tetraethoxytitanium, tetrabutoxytitanium, dichlorodimethoxytitanium, tetraisopropoxytitanium, titanium acetate and titanium acetylacetonate; phosphorus compounds, such as trimethylphosphine, triethylphosphine, tributylphosphine, triphenylphosphine, tributylmethylphosphonium halides, trioctylbutylphosphonium halides and triphenylmethylphosphonium halides; zirconium compounds, such as zirconium halides, zirconium acetylacetonate, zirconium alkoxides and zirconium acetate; lead and lead-containing compounds, e.g., lead oxides, such as PbO, $PbO_2$ and $Pb_3O_4$; lead sulfides, such as PbS, $Pb_2S_3$ and $PbS_2$; lead hydroxides, such as $Pb(OH)_2$, $Pb_3O_2(OH)_2$, $Pb_2[PbO_2(OH)_2]$ and $Pb_2O(OH)_2$; plumbites, such as $Na_2PbO_2$, $K_2PbO_2$, $NaHPbO_2$ and $KHPbO_2$; plumbates, such as $Na_2PbO_3$, $Na_2H_2PbO_4$, $K_2PbO_3$, $K_2[Pb(OH)_6]$, $K_4PbO_4$, $Ca_2PbO_4$ and $CaPbO_3$; lead carbonates and basic salts thereof, such as $PbCO_3$ and $2PbCO_3 \cdot Pb(OH)_2$; alkoxylead compounds and aryloxylead compounds, such as $Pb(OCH_3)_2$, $(CH_3O)Pb(OPh)$ and $Pb(OPh)_2$; lead salts of organic acids, and carbonates and basic salts thereof, such as $Pb(OCOCH_3)_2$, $Pb(OCOCH_3)_4$ and $Pb(OCOCH_3)_2 \cdot PbO \cdot 3H_2O$; organo-lead compounds, such as $Bu_4Pb$, $Ph_4Pb$, $Bu_3PbCl$, $Ph_3PbBr$, $Ph_3Pb$ (or $Ph_6Pb_2$), $Bu_3PbOH$ and $Ph_2PbO$ wherein Bu represents a butyl group and Ph represents a phenyl group; lead alloys, such as Pb—Na, Pb—Ca, Pb—Ba, Pb—Sn and Pb—Sb; lead minerals, such as galena and zinc blende; hydrates of these lead compounds; ion-exchangers, such as anion-exchange resins having tertiary amino groups, ion-exchange resins having amide groups, ion-exchange resins having at least one type of ion-exchange group selected from the group consisting of sulfonate, carboxylate and phosphate groups, and strongly basic solid anion-exchangers having quaternary ammonium groups as ion-exchange groups; and solid inorganic compounds, such as silica, silica-alumina, silica-magnesia, aluminosilicate, gallium silicate, various types of zeolites, various types of metal exchanged zeolites and ammonium-exchanged zeolites.

Among the above-mentioned solid catalysts, strongly basic anion-exchangers having quaternary ammonium groups as anion-exchange groups are preferred. Examples of such anion-exchangers include strongly basic anion-exchange resins having quaternary ammonium groups as anion-exchange groups, cellulose type strongly basic anion-exchangers having quaternary ammonium groups as anion-exchange groups, and strongly basic anion-exchangers carried on an inorganic carrier which have quaternary ammonium groups as anion-exchange groups.

Of these strongly basic anion-exchange resins having quaternary ammonium groups as ion-exchange groups, styrene type strongly basic anion-exchange resins and the like are preferred. A styrene type strongly basic anion-exchange resin is comprised of a styrene/divinylbenzene copolymer as a base resin, and quaternary ammonium groups (type I or type II) as anion-exchange groups, examples of which are diagrammatically represented by the following formulae (II).

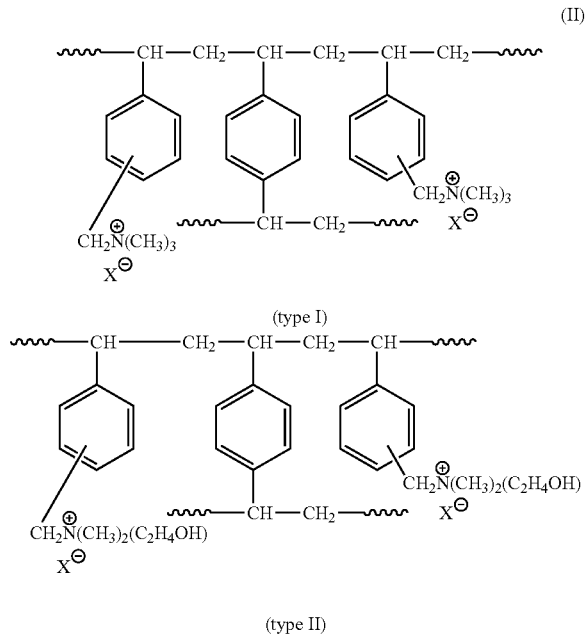

In above formulae (II), X represents an anion. Generally, X is at least one type of anion selected from the group consisting of $F^-$, $Cl^-$, $Br^-$, $I^-$, $HCO_3^-$, $CO_3^{2-}$, $CH_3CO_2^-$, $HCO_2^-$, $IO_3^-$, $BrO_3^-$ and $ClO_3^-$. It is preferred that X is selected from the group consisting of $Cl^-$, $Br^-$, $HCO_3^-$ and $CO_3^{2-}$. With respect to the structure of the base resin of the anion-exchange resin, either a gel type or a macroreticular type (MR type) can be used. However, because of the high resistance to organic solvents, the MR type is preferred.

Examples of cellulose type strongly basic anion exchangers having quaternary ammonium groups as ion exchange groups include cellulose type strongly basic anion-exchangers having ion-exchange groups of the structure represented by the formula: —OCH$_2$CH$_2$NR$_3$X, which exchangers are obtained by trialkylaminoethylation of a part or all of the hydroxyl groups of cellulose. In the above formula, R represents an alkyl group, for example, a methyl group, an ethyl group, a propyl group, a butyl group, preferably a methyl group or an ethyl group; and X is as defined above.

The inorganic carrier-carried strongly basic anion-exchanger usable in the present invention, which has quaternary ammonium groups as ion-exchange groups, is an anion-exchanger having quaternary ammonium groups represented by the formula —O(CH$_2$)$_n$NR$_3$X wherein R and X are as defined above and n is usually an integer of from 1 to 6, preferably 2, which anion-exchanger can be prepared by the modification of a part or all of the hydroxyl groups on the surface of the inorganic carrier. Examples of inorganic carriers include silica, alumina, silica-alumina, titania and zeolite. Of these, silica, alumina and silica-alumina are preferred. Silica is most preferred.

There is no limitation with respect to the method for the modification of hydroxyl groups on the surface of the inorganic carrier. For example, such a strongly basic anion-exchanger carried on an inorganic carrier can be obtained by subjecting an inorganic carrier and an aminoalcohol represented by the formula HO(CH$_2$)$_n$NR$_2$ to a dehydration reaction between them in the presence of a basic catalyst to thereby effect aminoalkoxylation, followed by the reaction of the resultant aminoalkoxylated inorganic carrier with an alkyl halide represented by the formula RX', wherein X' represents a halogen atom, preferably Cl, Br or I, to thereby convert the aminoalkoxy group into a —O(CH$_2$)$_n$NR$_3$X' group. The —O(CH$_2$)$_n$NR$_3$X' group is further converted to a —O(CH$_2$)$_n$NR$_3$X group having the desired anion X by an anion exchange reaction. When n is 2, an inorganic carrier is treated with N,N-dialkylaziridine so that the hydroxyl groups on the inorganic carrier are N,N-dialkylaminoethoxylated to obtain a —OCH$_2$CH$_2$NR$_2$ group, which is then converted to a —O(CH$_2$)NR$_3$X group by the above-mentioned method.

Commercially available solid, strongly basic anion-exchangers having quaternary ammonium groups as ion-exchange groups can be used in the present invention. When a commercially available solid, strongly basic anion-exchanger is used, it can be treated for anion-exchange with a desired anion species before it is used as a transesterification catalyst.

A solid catalyst comprised of a macroreticular or gel type organic polymer or an inorganic carrier, each having bonded thereto a heterocyclic group containing at least one nitrogen atom, is preferably used as a transesterification catalyst. Further, the above-mentioned solid catalyst can be treated for quaternarizing a part or all of the nitrogen-containing heterocyclic groups before it is used.

The amount of the transesterification catalyst to be used in the present invention varies depending on the type thereof. The homogeneous catalyst, which is soluble in the reaction system under the reaction conditions, is fed continuously in an amount of from 0.0001 to 50% by weight, based on the total weight of the raw material cyclic carbonate and the raw material aliphatic monohydric alcohol. When the solid catalyst is used, it is used generally in an amount of from 10 to 95% by volume, preferably from 50 to 90% by volume, based on the internal volume of the reactor. When the solid catalyst is packed in a distillation column, it is packed preferably in an amount of from 0.01 to 75% by volume, based on the internal volume of the empty distillation column.

When a multi-stage distillation column is used as a transesterification reactor, there is no particular restriction with respect to the method for continuously feeding a cyclic carbonate and an aliphatic monohydric alcohol to the continuous multi-stage distillation column. Any feeding method can be used as long as the feedstocks can be contacted with the catalyst in a region of the distillation column which corresponds to at least one stage, preferably at least two stages. That is, the cyclic carbonate and the aliphatic monohydric alcohol can be continuously fed to one or more stages of the continuous multi-stage distillation column through a desired number of feeding pipes at one or more desired locations as long as the above requirement is satisfied. The cyclic carbonate and the monohydric alcohol may be fed either to the same stage of the distillation column or to separate stages individually.

The feedstocks are continuously fed in a liquid form, a gaseous form or a gas-liquid mixture form. In addition to the feeding of the feedstocks to the continuous multi-stage distillation column as described above, additional feedstocks can be fed in a gaseous form to the lower portion of the distillation column intermittently or continuously. Also preferred is a method wherein the cyclic carbonate is continuously fed in a liquid form or a gas-liquid mixture form to a stage at a level higher than the stage where the catalyst is present, while the aliphatic monohydric alcohol is continuously fed to the lower portion of the distillation column in a gaseous form or a gas-liquid mixture form, or in a gaseous form and in a liquid form individually. In this case, some of the aliphatic monohydric alcohol may be contained in the cyclic carbonate.

In the present invention, a small amount of a diol as a desired product may be contained in the raw materials. Further, the aliphatic monohydric alcohol may contain a concomitant dialkyl carbonate. When the aliphatic monohydric alcohol contains a concomitant dialkyl carbonate, the amount of the concomitant dialkyl carbonate in the aliphatic monohydric alcohol is generally in the range of from 0 to 40% by weight, preferably from 0.1 to 30% by weight, more preferably from 1 to 20% by weight, based on the total weight of the aliphatic monohydric alcohol and the concomitant dialkyl carbonate.

The ratio of the aliphatic monohydric alcohol to the cyclic carbonate to be fed to the transesterification reactor may vary depending on the type and quantity of the transesterification catalyst and the reaction conditions, but, in general, the molar ratio of the aliphatic monohydric alcohol to the cyclic carbonate may be in the range of from 0.01 to 1,000. For increasing the conversion of the cyclic carbonate, it is preferred to feed the aliphatic monohydric alcohol in an excess amount which is 2 times or more by mole the mole of the cyclic carbonate. However, too high a concentration of the aliphatic monohydric alcohol is undesirable because the size of the reaction equipment needs to be large. Therefore, it is especially preferred to use the aliphatic monohydric alcohol in an amount which is 2 to 20 times by mole the mole of the cyclic carbonate.

When carbon dioxide is present in a high concentration in the transesterification reaction system of the method of the present invention, the reaction rate becomes low. Therefore, the CO$_2$ concentration of the reaction system is generally not higher than 500 ppm by weight, preferably not higher than 200 ppm by weight, more preferably not higher than 100 ppm by weight.

Also when water is present in a high concentration in the transesterification reaction system of the method of the present invention, hydrolysis of a cyclic carbonate takes place simultaneously with the transesterification, resulting in a decrease in the selectivity for dialkyl carbonate. Therefore, the water concentration of the reaction system is generally not higher than 200 ppm by weight, preferably not higher than 100 ppm by weight.

In the method of the present invention, when it is attempted to render the conversion of the cyclic carbonate close to 100%, the reaction time needs to be prolonged, and the aliphatic monohydric alcohol needs to be used in large excess. On the other hand, when the conversion of the cyclic carbonate is too low, the size of the apparatus used for separation removal of the unreacted cyclic carbonate needs to be large. Therefore, the conversion of the cyclic carbonate is generally in the range of from 95 to 99.999%, preferably from 98 to 99.99%, more preferably from 99 to 99.99%.

In the present invention, the dialkyl carbonate which is one of the products of the pre-sent invention is withdrawn from the transesterification reactor. In general, the dialkyl carbonate is withdrawn from the upper portion of the transesterification reactor as a low boiling point mixture in a gaseous form. The low boiling point mixture withdrawn from the upper portion of the reactor may be the dialkyl carbonate alone or a mixture of the dialkyl carbonate and the aliphatic monohydric alcohol. Further, the withdrawn gaseous mixture may also contain a high boiling point product in a small amount.

When a multi-stage distillation column is used as a transesterification reactor, a withdrawal port of the continuous multi-stage distillation column for withdrawing the gaseous low boiling point mixture containing the dialkyl carbonate is preferably provided at a position between the position from which the feedstocks are fed and the top of the distillation column, or in the top of the distillation column. It is more preferred to provide the withdrawal port for the low boiling point mixture in the top of the distillation column. A part of the low boiling point mixture withdrawn from the withdrawal port may be returned to the upper portion of the distillation column to thereby effect the so-called reflux operation. When the reflux ratio is increased by conducting this reflux operation, the distillation efficiency of a low boiling product into a vapor phase is increased, thereby advantageously increasing the concentration of a low boiling point product in the withdrawn gaseous component. However, too much of an increase in the reflux ratio disadvantageously leads to an increase in the thermal energy required. Thus, the reflux ratio is generally chosen in the range of from 0 to 10, preferably from 0 to 5, more preferably from 0 to 3.

By continuously feeding the low boiling point mixture withdrawn from the upper portion of the transesterification reactor, containing the dialkyl carbonate, to a dialkyl carbonate separation apparatus and continuously recovering the dialkyl carbonate from the separation apparatus, the product dialkyl carbonate can be obtained. Examples of such dialkyl carbonate separation apparatuses include a distillation type separation apparatus, an extractive distillation type separation apparatus, a liquid-liquid extraction type separation apparatus, a crystallization type separation apparatus, an adsorption type separation apparatus and a membrane type separation apparatus. A combination of a plurality of different or identical separation apparatuses may be used. Among these separation apparatuses, a distillation type separation apparatus is especially preferred.

When the low boiling point mixture (containing the dialkyl carbonate and the unreacted aliphatic monohydric alcohol) withdrawn from the upper portion of the multi-stage distillation column is subjected to separation by means of a distillation type separation apparatus, the low boiling point mixture can be separated into various components, such as the dialkyl carbonate and the unreacted aliphatic monohydric alcohol, wherein some of the separated components are obtained in the form of one or more column top fractions containing a single component or a plurality of components and some of the separated components are obtained in the form of a column bottom liquid. As the above-mentioned column top fraction, an azeotropic mixture may be obtained depending on the types of feedstocks. After the components in the low boiling point mixture withdrawn from the upper portion of the multi-stage distillation column are separated by means of a distillation type separation apparatus, one or more fractions containing the unreacted aliphatic monohydric alcohol and/or a column bottom liquid containing the unreacted aliphatic monohydric alcohol is then fed to the transesterification reactor.

As the distillation type separation apparatus, a single continuous multi-stage distillation column or a plurality of continuous multi-stage distillation columns can be used, wherein each continuous multi-stage distillation column may be of the same type as used as the transesterification reactor. Explained hereinbelow is a mode of the method of the present invention in which an aliphatic monohydric alcohol and a dialkyl carbonate form a minimum boiling point azeotropic mixture, and wherein dimethyl carbonate is produced by using methanol as the aliphatic monohydric alcohol. A low boiling point mixture (containing methanol and dimethyl carbonate) withdrawn from the upper portion of the transesterification reactor is continuously fed to a dimethyl carbonate separation column. A low boiling point mixture containing a minimum boiling point azeotropic mixture of methanol and dimethyl carbonate is continuously withdrawn from an upper portion of the dimethyl carbonate separation column, while continuously withdrawing dimethyl carbonate from a lower portion of the dimethyl carbonate separation column, thereby obtaining dimethyl carbonate.

As the dimethyl carbonate separation column, a single continuous multi-stage distillation column or a plurality of continuous multi-stage distillation columns can be used, wherein each continuous multi-stage distillation column may be of the same type as used as the trans-esterification reactor. The dimethyl carbonate separation column is generally operated under reduced pressure, atmospheric pressure or super-atmospheric pressure, specifically in the range of from 0.5× $10^5$ to $50×10^5$ Pa (0.51 to 51 kg/cm$^2$) in terms of the absolute pressure.

The composition of methanol/dimethyl carbonate minimum boiling point azeotropic mixture may be varied depending on the operating pressure of the dimethyl carbonate separation column. Therefore, the operating pressure of the dimethyl carbonate separation column is chosen so that the dimethyl carbonate is obtained from the lower portion of the dimethyl carbonate separation column. Specifically, an operating pressure higher than an operating pressure corresponding to the methanol/dimethyl carbonate ratio of the low boiling point mixture withdrawn from the upper portion of the transesterification reactor is chosen for the dimethyl carbonate separation column.

The dialkyl carbonate obtained by the method of the present invention contains a carbonate ether represented by the above-mentioned formula (2). The lower the cyclic ether content of the cyclic carbonate, the lower the carbonate ether content of the dialkyl carbonate produced. However, for producing a cyclic carbonate having extremely low cyclic ether content, the cyclic carbonate must be produced by a complicated method which is not practical for commercial production. Therefore, in the present invention, the cyclic ether content of the dialkyl carbonate produced is not more than 10,000 ppm, preferably in the range of from 1 to 10,000 ppm, more preferably from 3 to 5,000 ppm, still more preferably from 10 to 3,000 ppm.

The low boiling point mixture (containing a minimum boiling point azeotropic mixture of methanol and dimethyl carbonate) withdrawn from the upper portion of the above-mentioned dimethyl carbonate separation column may be fed to the transesterification reactor as a feedstock usable in the present invention.

In the method of the present invention, the upper portion of the continuous multi-stage distillation column means a portion between the top of the distillation column and a position at approximately half the height of the distillation column, and the upper portion includes the top of the column. The lower portion of the continuous multi-stage distillation column means a portion between the bottom of the distillation column and a position at approximately half the height of the distillation column, and the lower portion includes the bottom of the column.

Further, in the method of the present invention, the diol produced in the transesterification reactor is obtained as the high boiling point mixture withdrawn in a liquid form from the lower portion of the transesterification reactor. The high boiling point mixture contains the produced diol and the unreacted cyclic carbonate, and may also contain a part of the unreacted aliphatic monohydric alcohol or both a part of the unreacted aliphatic monohydric alcohol and a part of the produced dialkyl carbonate.

The withdrawal port for withdrawing the high boiling point mixture (containing the produced diol) in the liquid form from the transesterification reactor is positioned at a lower portion of the reactor, preferably at the bottom of the reactor. A part of the withdrawn liquid mixture may be recycled to the lower portion of the transesterification reactor in a gaseous form or a gas-liquid mixture form by heating by means of a reboiler.

When a multi-stage distillation column is used as a transesterification reactor, the rate at which a liquid flows down inside the continuous multi-stage distillation column and the rate at which a vapor ascends inside the distillation column may be varied depending on the type of the distillation column, and on the type of the packing in the case of a packed column. However, the distillation column is generally operated so that no flooding or weeping occurs.

In the method of the present invention, the average residence time of the liquid phase in the transesterification reactor depends on the reaction conditions, and the type and inner structure (for example, the types of the plate and packing) of the transesterification reactor, but is generally in the range of from 0.001 to 50 hours, preferably from 0.01 to 10 hours, more preferably from 0.05 to 5 hours.

The reaction temperature varies depending on the types of the raw materials and the reaction pressure, but is generally chosen in the range of from −20 to 350° C., preferably from 0 to 200° C. The reaction pressure in the transesterification reactor can be selected from reduced pressure, atmospheric pressure and superatmospheric pressure. The reaction pressure is generally in the range of from 1 Pa to $2\times10^6$ Pa, preferably from $1\times10^3$ Pa to $1\times10^6$ Pa, more preferably from $1\times10^4$ Pa to $5\times10^5$ Pa, in terms of the absolute pressure.

It is also possible to supply a part of the high boiling point mixture withdrawn in a liquid form from the lower portion of the transesterification reactor to the transesterification reactor, so that a part of the unreacted cyclic carbonate and/or a part of the unreacted aliphatic monohydric alcohol can be recycled to the transesterification reactor.

When the high boiling point mixture (containing the produced diol) withdrawn from the lower portion of the transesterification reactor is subjected to separation in the diol purification step, the high boiling point mixture can be separated into various components. In general, (i) when the high boiling point mixture contains low boiling point components (such as an aliphatic alcohol used as a raw material), it is preferred that, before the diol purification step, an aliphatic alcohol and the like are separated from the high boiling point mixture by distillation or the like and, then, the separated aliphatic alcohol and the like are recycled to the transesterification reactor, and (ii) it is also preferred that, before the diol purification step, the unreacted cyclic carbonate contained in the high boiling point mixture is separated therefrom and, then, the remaining part of high boiling point mixture is introduced into the diol purification step. As methods for separating unreacted cyclic carbonate from the high boiling point mixture, there can be mentioned (ii-1) separation by distillation, (ii-2) hydrolysis to convert unreacted cyclic carbonate to a diol, and (ii-3) elimination of unreacted cyclic carbonate by the etherification of the cyclic carbonate with a diol. The etherification is especially preferred in the present invention.

Specifically, as preferred examples of manners in which the high boiling point mixture withdrawn from the transesterification reactor is treated before subjected to a step for the purification of diol, the following two modes can be mentioned.

1. A mode in which the high boiling point mixture (in the liquid form) withdrawn from the lower portion of the transesterification reactor contains the low boiling point mixture (including a part of the unreacted aliphatic monohydric alcohol and dialkyl carbonate), and wherein the high boiling point mixture is continuously introduced, prior to the feeding thereof to the continuous etherification reactor, to a low boiling point mixture separation column which is comprised of a continuous multi-stage distillation column, and wherein a low boiling point mixture containing the part of the unreacted aliphatic monohydric alcohol and dialkyl carbonate which is contained in the high boiling point mixture is continuously withdrawn from an upper portion of the low boiling point mixture separation column, while continuously withdrawing a high boiling point mixture containing the diol and the unreacted cyclic carbonate from the low boiling point mixture separation column through one or more side-cut withdrawal ports provided in a side wall of the column at one or more positions thereof corresponding to one or more stages selected from the group consisting of intermediate stages and a lowermost stage of the low boiling point mixture separation column, wherein the low boiling point mixture withdrawn from the upper portion of the low boiling point mixture separation column is continuously recycled to the transesterification reactor, while continuously feeding the high boiling point mixture withdrawn through the side-cut withdrawal port of the low boiling point mixture separation column to the diol separation apparatus.

As the low boiling point mixture separation column, a continuous multi-stage distillation column can be used, and the continuous multi-stage distillation column may be of the same type as used as the transesterification reactor.

2. A mode in which the high boiling point mixture withdrawn from the lower portion of the transesterification reactor contains a part of the unreacted aliphatic monohydric alcohol and dialkyl carbonate, and wherein the high boiling point mixture is continuously introduced, prior to the feeding thereof to the etherification reactor, to a low boiling point mixture separation column which is comprised of a continuous multi-stage distillation column, and wherein a low boiling point mixture containing the part of the unreacted aliphatic monohydric alcohol and dialkyl carbonate which is contained in the high boiling point mixture is continuously withdrawn from an upper portion of the low boiling point mixture separation column, while continuously withdrawing a high boiling point mixture containing the diol and the unreacted cyclic carbonate from a lower portion of the low boiling point mixture separation column, followed by the etherification of the cyclic carbonate in the withdrawn high boiling point mixture at the bottom portion of the low boiling point mixture separation column, wherein the low boiling point mixture withdrawn from the upper portion of the low boiling point mixture separation column is continuously recycled to the transesterification reactor, while continuously feeding the high boiling point mixture containing the diol and the ether to the diol separation apparatus.

The above-mentioned etherification can be performed in accordance with the etherification method described in Patent Document 21. Specifically, the high boiling point mixture containing the produced diol and the unreacted cyclic carbonate is fed to an etherification reactor, to thereby effect an etherification reaction between the unreacted cyclic carbonate and a part of the produced diol and produce a chain ether represented by the following formula:

$$HO(R^1O)_nH$$

wherein $R^1$ is as defined for formula (1) above.

The reaction conditions for the etherification reaction in the etherification reactor may be varied depending on the presence or absence of an etherification catalyst. When an etherification catalyst is used, the etherification reaction conditions may be varied depending on the type and amount of the etherification catalyst. However, in general, the reaction temperature is from 50 to 350° C., preferably from 80 to 300° C., more preferably from 100 to 250° C. The reaction time may be varied depending on the presence or absence of an etherification catalyst. When an etherification catalyst is used, the reaction time may be varied depending on the type and amount of the etherification catalyst and the reaction temperature. However, in general, the reaction time is from 0.001 to 50 hours, preferably from 0.01 to 10 hours, more preferably from 0.02 to 5 hours, in terms of the average residence time. The reaction pressure may be varied depending on the reaction temperature. However, in general, the reaction pressure is from $1\times10^3$ to $2\times10^7$ Pa, preferably from $1\times10^4$ to $1\times10^7$ Pa, in terms of the absolute pressure.

The conversion of the cyclic carbonate in the etherification reaction is generally from 90 to 100%, preferably from 95 to 100%, more preferably from 98 to 100%.

When carbon dioxide enters the transesterification reactor, the transesterification reaction is adversely affected, so that the reaction rate becomes low. Therefore, when the etherification reaction mixture withdrawn from the etherification reactor contains carbon dioxide, it is preferred that the carbon dioxide is separated from the etherification reaction mixture by means of a carbon dioxide separation apparatus.

In addition, there can be used the distillation separation method described in Patent Documents 22 and 23. In this method, water is fed to the distillation separation apparatus in which a reaction mixture containing diol is subjected to distillation separation.

In the method of the present invention, it is not necessary to use a solvent. However, for the purposes of, e.g., (1) facilitating the reaction operation and (2) separating a dialkyl carbonate and a diol efficiently by performing azeotropic distillation or extractive distillation, an appropriate inert solvent may be used as a reaction solvent. Examples of inert solvents include an ether, an aliphatic hydrocarbon, an aromatic hydrocarbon, a halogenated aliphatic hydrocarbon and a halogenated aromatic hydrocarbon.

An inert gas, such as nitrogen, helium, argon or the like, may be present in the reaction system. Further, for the purpose of promoting the distilling off of a generated low boiling point reaction product, the above-mentioned inert gas or a gaseous form of an inert low boiling point organic compound may be introduced to the reaction system from a lower portion of a continuous multi-stage distillation column.

EXAMPLES

Hereinbelow, the present invention will be described in more detail with reference to the following Examples and Comparative Example, which should not be construed as limiting the scope of the present invention.

In the following Examples and Comparative Example, the yield (%) of ethylene glycol is determined, based on the amount of the charged ethylene carbonate; the selectivity (%) for ethylene glycol is determined, based on the amount of the consumed ethylene carbonate; the yield (%) of dimethyl carbonate is determined, based on the amount of the charged ethylene carbonate; and the selectivity (%) for dimethyl carbonate is determined, based on the amount of the consumed methanol. The positions of respective stages of a distillation column are represented by the ordinal numbers for the respective stages as counted from the top stage of the distillation column.

Example 1

Using a production system as shown in FIG. 1, dimethyl carbonate (DMC) and ethylene glycol (EG) were continuously produced from ethylene carbonate (EC) and methanol (MeOH). Continuous multi-stage distillation column 1 was comprised of a 60-stage Oldershaw distillation column which has an inner diameter of 5 cm. EC (containing 400 ppm of ethylene oxide) was continuously fed in a liquid form to distillation column 1 at the fifth stage thereof through conduit 2 and preheater 3 at a flow rate of 231 g/h, and an 18% by weight solution of potassium hydroxide (as a catalyst) in ethylene glycol was also continuously fed in a liquid form to distillation column 1 at the fifth stage thereof through conduit 2' at a flow rate of 1.1 g/h, while continuously feeding a mixture of MeOH and DMC (MeOH/DMC weight ratio=97/3) in a liquid form to distillation column 1 at the 30th stage thereof through conduit 5 and preheater 6 at a flow rate of 735.0 g/h, to thereby effect a transesterification reaction. Continuous multi-stage distillation column 1 was operated under conditions wherein the reaction pressure and reaction temperature, each as measured at column top 4 thereof, were atmospheric pressure and 63.8° C., respectively.

A low boiling point mixture in a gaseous form distilled from column top 4 of distillation column 1 was condensed by condenser 7. A part of the resultant condensate was refluxed to column top 4 of distillation column 1 through conduit 8 (reflux ratio: 0.4), while the remainder of the condensate (hereinbelow, the condensate is referred to simply as "column top condensate from column 1") was fed to DMC separation column 71 at a position 80 cm below the top of column 71 through conduit 9 at a flow rate of 803.1 g/h, wherein column 71 was comprised of a packed column type distillation column having an inner diameter of 2.5 cm and a packing height of 160 cm and having packed therein Dixon packings (3 mmφ). The column top condensate from column 1 contained MeOH and DMC in concentrations of 67.9% by weight and 32.1% by weight, respectively.

On the other hand, a liquid was withdrawn from column bottom 10 of distillation column 1 through conduit 11 (hereinbelow, the liquid is referred to simply as "bottom liquid of column 1"), and a part of the bottom liquid of column 1 was heated by reboiler 12 to provide the energy required for distillation and returned to column bottom 10 of distillation column 1 through conduit 13, while the remainder of the bottom liquid of column 1 was withdrawn as a high boiling point mixture in a liquid form, and fed to low boiling point mixture separation column 17 at a position 100 cm below the top of column 17 through conduit 14 at a flow rate of 231.3 g/h, wherein column 17 was comprised of a packed column type distillation column having an inner diameter of 2.5 cm and a packing height of 160 cm and having packed therein Dixon packings (3 mmφ). The high boiling point mixture contained EG, MeOH, EC, DMC and KOH in concentrations of 70.7% by weight, 29.1% by weight, 0.099% by weight, 0.04% by weight and 0.086% by weight, respectively. The conversion of EC in the transesterification reaction was 99.9%.

DMC separation column 71 was operated under conditions wherein the pressure of column top 72 thereof was $1.4 \times 10^6$ Pa and the temperature of column bottom 73 thereof was 205° C. A low boiling point mixture in a gaseous form distilled from column top 72 of column 71 was condensed by condenser 75. A part of the resultant condensate was refluxed to column top 72 of column 71 through conduit 77 (reflux ratio: 2), while feeding the remainder of the condensate to continuous multi-stage distillation column 1 through conduit 78 (which is connected to conduit 5), conduit 5 and preheater 6. For stabilizing the composition of the liquid fed to continuous multi-stage distillation column 1 through conduit 5, the composition of the liquid fed to continuous multi-stage distillation column 1 through conduit 5 was gradually changed from MeOH/DMC to only MeOH.

A liquid was withdrawn from column bottom 73 of DMC separation column 71 through conduit 79 (hereinbelow, the liquid is referred to simply as "bottom liquid of column 71"), and a part of the bottom liquid of column 71 was heated by reboiler 80 to provide the energy required for distillation and returned to column bottom 73 of distillation column 71 through conduit 81, while the remainder was withdrawn at a flow rate of 235 g/h from the production system through conduit 82. The bottom liquid of column 71 contained 99.9% by weight of DMC and 1,150 ppm of carbonate ether ($CH_3OCH_2CH_2OCOOCH_3$).

Low boiling point mixture separation column 17 was operated under conditions wherein the pressure of column top 18 thereof was atmospheric pressure and the temperature of column bottom 26 thereof was 201° C. At the column bottom 26 of low boiling point mixture separation column 17, an etherification reaction between EC and EG was effected, thereby forming diethylene glycol (DEG). The residence time at column bottom 26 of low boiling point mixture separation column 17 was 1.5 hours. A low boiling point mixture in a gaseous form distilled from column top 18 of column 17 was condensed by condenser 19. A part of the resultant condensate was refluxed to column top 18 of column 17 through conduit 20 (reflux ratio: 1), while feeding the remainder of the condensate to an upper portion of carbon dioxide separation column 22 through conduit 21. From conduit 23 provided at the bottom of carbon dioxide separation column 22, nitrogen gas was introduced into the condensate, thereby bubbling the condensate with the nitrogen gas. The nitrogen gas entraining carbon dioxide was discharged from conduit 24 provided at the top of column 22. The resultant carbon dioxide-free liquid obtained in column 22 was withdrawn from conduit 25 provided at a lower portion of column 22, and recycled to continuous multi-stage distillation column 1 at the 30th stage thereof at a flow rate of 70.2 g/h.

A liquid was withdrawn from the bottom of low boiling point mixture separation column 17 (hereinbelow, the liquid is referred to simply as "bottom liquid of column 17"). The bottom liquid of column 17 contained EG and DEG in concentrations of 67.6% by weight and 17.3% by weight, respectively. The bottom liquid of column 17 was withdrawn at a flow rate of 163.9 g/h through conduit 30 as an etherification reaction mixture, while the remainder of the bottom liquid of column 17 was heated by reboiler 28 and returned to column bottom 26 of column 17 through conduit 29. The etherification reaction mixture contained EG and DEG in concentrations of 99.7% by weight and 0.17% by weight, respectively (EC was not detected).

The etherification reaction mixture was fed to EG purification column 41 at a position 90 cm below the top of column 41 through conduit 30, wherein column 41 was comprised of a packed column type distillation column having an inner diameter of 2.5 cm and a packing height of 120 cm and having packed therein Dixon packings (3 mmφ).

EG purification column 41 was operated under conditions wherein the pressure of column top 42 thereof was 4,000 Pa (30 torr) and the temperature of column bottom 43 thereof was 123.5° C. A distillate was withdrawn in a liquid form through conduit 56 provided at a position 50 cm below the top of column 41 at a flow rate of 160.9 g/h, to thereby obtain a side-cut distillate. A mixture distilled from column top 42 of column 41 was condensed by condenser 45. A part of the resultant condensate was refluxed to column top 42 of column 41 through conduit 47 (reflux ratio: 2), while withdrawing the remainder of the condensate through conduit 48. A liquid was withdrawn from the bottom of EG purification column 41 through conduit 49 (hereinbelow, the liquid is referred to simply as "bottom liquid of column 41"). The bottom liquid of column 41 contained EG and DEG in concentrations of 65.2% by weight and 20.3% by weight, respectively. 2.8 g of the bottom liquid of column 41 was withdrawn every two hours from the production system through conduit 52, while the remainder of the bottom liquid of column 41 was returned to column bottom 43 of column 41 through reboiler 50 and conduit 51.

From the above data, it can be seen that the yield of DMC (containing 1,150 ppm of carbonate ether) was 99.8%, the selectivity for DMC was not lower than 99%, and EG was obtained in a yield of 99.8%.

The above-obtained DMC and phenol were subjected to a transesterification reaction, thereby obtaining diphenyl carbonate (DPC). 235 g of the obtained DPC and 228 g of bisphenol A were charged into a vacuum reactor equipped with a stirrer. The atmosphere in the vacuum reactor was purged with nitrogen gas, and the temperature was gradually elevated from 180° C. to 220° C. while stirring. Thereafter, the vacuum reactor was hermetically closed. Then, polymerization was performed while stirring at 100 rpm under a pressure of 8,000 Pa for 30 minutes and, then, under a pressure of 4,000 Pa for 90 minutes. Subsequently, the temperature was elevated to 270° C., and further polymerization was performed under a pressure of 70 Pa for 1 hour, thereby obtaining an aromatic polycarbonate. The obtained aromatic polycarbonate was colorless and transparent, which is good. The number average molecular weight was 10,500.

Comparative Example 1

Production of DMC and EG was performed in substantially the same manner as in Example 1 except that the ethylene oxide content of EC used as a raw material was changed to 5,000 ppm. As a result, there were obtained DMC (containing 15,300 ppm of carbonate ether) and EG, wherein the yield of DMC was 96.4%, the selectivity for DMC was 95.2%, and the yield of EG was 94.3%. From the obtained DMC, DPC was produced in the same manner as in Example 1. From the obtained DPC, an aromatic polycarbonate was produced in the same manner as in Example 1. The obtained aromatic polycarbonate was discolored to assume a yellow color and had a number average molecular weight of 6,300. A comparison between the results of Example 1 and the results of this Comparative Example 1 shows that, from a cyclic carbonate containing a large amount of a cyclic ether, a dialkyl carbonate containing a high concentration of a carbonate ether is obtained, and that, from such a dialkyl carbonate containing a high concentration of a carbonate ether, it is impossible to obtain highly reactive diphenyl carbonate necessary for producing a high molecular weight aromatic polycarbonate.

Example 2

Production of DMC and EG was performed in substantially the same manner as in Example 1 except that the ethylene oxide content of EC used as a raw material was changed to 1,200 ppm. As a result, there were obtained DMC (containing 3,400 ppm of carbonate ether) and EG, wherein the yield of DMC was 99.6%, the selectivity for DMC was not lower than 99%, and the yield of EG was 99.6%. From the obtained DMC, DPC was produced in the same manner as in Example 1. From the obtained DPC, an aromatic polycarbonate was produced in the same manner as in Example 1. The obtained aromatic polycarbonate was colorless and had a number average molecular weight of 10,200.

Example 3

Production of DMC and EG was performed in substantially the same manner as in Example 1 except that the ethylene oxide content of EC used as a raw material was changed to 2,000 ppm. As a result, there were obtained DMC (containing 5,600 ppm of carbonate ether) and EG, wherein the yield of DMC was 99.2%, the selectivity for DMC was not lower than 99%, and the yield of EG was 99.1%. From the obtained DMC, DPC was produced in the same manner as in Example 1. From the obtained DPC, an aromatic polycarbonate was produced in the same manner as in Example 1. The obtained aromatic polycarbonate was colorless and had a number average molecular weight of 9,100.

INDUSTRIAL APPLICABILITY

In the dialkyl carbonate produced by the method of the present invention, the content of a carbonate ether (which is a conventionally unknown impurity) is reduced to a specific low range. The dialkyl carbonate obtained by the method of the present invention can be used to produce a transesterification aromatic carbonate. The transesterification aromatic carbonate produced can be very advantageously used to produce a colorless, high molecular weight aromatic polycarbonate.

The invention claimed is:

1. A dialkyl carbonate produced by a method comprising:
   (a) effecting a transesterification reaction between a cyclic carbonate and an aliphatic monohydric alcohol in the presence of a transesterification catalyst, thereby obtaining a reaction mixture containing a product dialkyl carbonate and a product diol represented by the formula: HO—$R^1$—OH wherein $R^1$ is as defined below for the formula (1),
   (b) withdrawing a dialkyl carbonate-containing liquid from said reaction mixture, followed by separation of the dialkyl carbonate from the dialkyl carbonate-containing liquid, and
   (c) withdrawing a diol-containing liquid from said reaction mixture, followed by separation of the diol from the diol-containing liquid,
   said steps (b) and (c) being performed in either order or simultaneously,
   wherein:
   said cyclic carbonate contains a cyclic ether represented by the formula (1) below in an amount of from 0.1 to 3,000 ppm by weight, and
   said product dialkyl carbonate contains a carbonate ether represented by the formula (2) below in an amount of not more than 10,000 ppm by weight,

(1)

wherein $R^1$ represents a divalent group represented by the formula: —$(CH_2)_m$— wherein m is an integer of from 2 to 6, and at least one hydrogen atom of $R^1$ is optionally replaced by at least one substituent group selected from the group consisting of a $C_{1-10}$ alkyl group and a $C_{6-10}$ aryl group, and

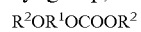
(2)

wherein $R^1$ is as defined above for formula (1), $R^2$ represents a $C_{1-12}$ monovalent aliphatic group, and at least one hydrogen atom of $R^2$ is optionally replaced by at least one substituent group selected from the group consisting of a $C_{1-10}$ alkyl group and a $C_{6-10}$ aryl group.

2. The dialkyl carbonate according to claim 1, wherein the amount of said cyclic ether in said cyclic carbonate is from 3 to 1,500 ppm by weight.

3. The dialkyl carbonate according to claim 2, wherein the amount of said cyclic ether in said cyclic carbonate is from 10 to 1,000 ppm by weight.

4. The dialkyl carbonate according to claim 1, wherein said cyclic carbonate is ethylene carbonate.

5. The dialkyl carbonate according to claim 1, which contains a carbonate ether represented by the formula (2) of claim 1 in an amount of from 1 to 10,000 ppm by weight.

6. The dialkyl carbonate according to claim 5, wherein the amount of said carbonate ether in the dialkyl carbonate is from 3 to 5,000 ppm by weight.

7. The dialkyl carbonate according to claim 6, wherein the amount of said carbonate ether in the dialkyl carbonate is from 10 to 3,000 ppm by weight.

8. The dialkyl carbonate according to any one of claims 1 to 7, wherein said transesterification reaction is performed in a reactive distillation column.

* * * * *